(12) United States Patent
Shiue

(10) Patent No.: US 8,707,522 B2
(45) Date of Patent: Apr. 29, 2014

(54) BUCKLING DEVICE

(75) Inventor: Chih-Cheng Shiue, Taipei (TW)

(73) Assignee: QBAS Co., Ltd., Taipei (TW)

( * ) Notice: Subject to any disclaimer, the term of this patent is extended or adjusted under 35 U.S.C. 154(b) by 155 days.

(21) Appl. No.: 12/890,666

(22) Filed: Sep. 26, 2010

(65) Prior Publication Data
US 2011/0138588 A1    Jun. 16, 2011

(51) Int. Cl.
*A44B 11/06* (2006.01)
*A44B 11/25* (2006.01)

(52) U.S. Cl.
USPC ............................. 24/170; 24/193; 24/593.11

(58) Field of Classification Search
USPC .................. 24/168, 170, 178, 188, 191, 193, 24/265 BC, 16 PB, 17 AP, 594.1, 594.11, 24/163 R, 164, 68 E, 593.11, 633, 587.1, 24/587.12
See application file for complete search history.

(56) References Cited

U.S. PATENT DOCUMENTS

| | | | | |
|---|---|---|---|---|
| 4,727,630 A * | 3/1988 | Alan | ............................ | 24/593.11 |
| 6,219,889 B1 * | 4/2001 | Lovato et al. | ................ | 24/587.1 |
| 6,457,210 B1 * | 10/2002 | Shirai et al. | ................... | 24/16 PB |
| 6,925,020 B2 * | 8/2005 | Kwon | ............................ | 365/205 |
| 6,966,102 B2 * | 11/2005 | Shiue | ............................... | 24/196 |
| 7,007,311 B2 * | 3/2006 | Chiang | ............................. | 2/448 |
| 7,162,778 B2 * | 1/2007 | Pan | .................................. | 24/170 |
| 7,458,134 B2 * | 12/2008 | Shiue | ............................ | 24/68 E |
| 7,571,520 B2 * | 8/2009 | Shiue | ......................... | 24/265 BC |
| 7,631,400 B2 * | 12/2009 | Chiang | ............................ | 24/170 |
| 7,640,633 B2 * | 1/2010 | Chou | ............................. | 24/68 E |
| 7,665,190 B2 * | 2/2010 | Weng | .............................. | 24/170 |
| 7,836,561 B2 * | 11/2010 | Vaccaro et al. | ............... | 24/68 E |
| 7,921,523 B2 * | 4/2011 | Chou | .............................. | 24/170 |
| 7,966,701 B2 * | 6/2011 | Shiue | .............................. | 24/170 |
| 8,042,199 B2 * | 10/2011 | Chiang | ............................ | 2/448 |
| 2006/0010585 A1 | 1/2006 | Chiang | | |
| 2006/0230584 A1 | 10/2006 | Pan | | |

(Continued)

FOREIGN PATENT DOCUMENTS

| | | |
|---|---|---|
| CN | 201253450 | 6/2009 |
| FR | 2679342 | 1/1993 |

(Continued)

OTHER PUBLICATIONS

First office Action for the Chinese counterpart (CN200910162684.4) Chinese version and machine translated version, Dec. 16, 2011.
China Office Action mailed Aug. 10, 2012.
Machine translation of summary of Chinese Office Action mailed Aug. 10, 2012.

(Continued)

*Primary Examiner* — Robert J Sandy
*Assistant Examiner* — Abigail Morrell
(74) *Attorney, Agent, or Firm* — McClure, Qualey & Rodack, LLP

(57) ABSTRACT

A buckling device for fastening a belt is provided. The buckling device comprises a first portion, a second portion, an elastic portion and at least one push portion. The elastic portion is disposed between the first portion and the second portion. The second portion engages with the belt and the belt is fastened. The at least one push portion is integrally formed with the elastic portion and is exposed from the first portion and the second portion. The at least one push portion is adapted to be pushed inwards by an external force to force the elastic portion to extrude outwards so that the second portion is forced to move outwards to release the belt.

11 Claims, 16 Drawing Sheets

(56) References Cited

U.S. PATENT DOCUMENTS

| | | | | |
|---|---|---|---|---|
| 2007/0256283 A1* | 11/2007 | Chiang | | 24/193 |
| 2008/0244875 A1* | 10/2008 | Chou | | 24/170 |
| 2008/0289160 A1* | 11/2008 | Chou | | 24/68 R |
| 2009/0100645 A1* | 4/2009 | Weng | | 24/170 |
| 2009/0276942 A1* | 11/2009 | Chiang | | 2/452 |

FOREIGN PATENT DOCUMENTS

| | | |
|---|---|---|
| GB | 2416598 | 2/2006 |
| GB | 2416598 A | 2/2006 |
| JP | 06-237805 | 8/1994 |
| JP | 2001-198236 | 7/2001 |
| JP | 2001-218869 | 8/2001 |
| TW | M340997 | 9/2008 |

OTHER PUBLICATIONS

European search report of the parallel EP Application No. 10 187 216.6 (search report bears an official mailing date of Apr. 5, 2012).

Japanese office action of the relevant JP Application No. 2010-018631 (that office action bears an official mailing date of Mar. 6, 2012; JP Application No. 2010-018631 is parallel to U.S. Appl. No. 12/685,783).

European search report of a relevant EP Application No. 10 15 095.6 (that office action bears an official mailing date of May 8, 2012: EP Application No. 10 15 095.6 is parallel to U.S. Appl. No. 12/685,783).

Taiwan office action of a relevant TW Application No. 098126724 (that office action bears an official mailing date of Jun. 29, 2012; TW Application No. 098126724 is parallel to U.S. Appl. No. 12/685,783).

* cited by examiner

BUCKLING DEVICE

This application claims the benefit from the priorities of Taiwan Utility Model Application No. 098222723 filed on Dec. 4, 2009, and Taiwan Utility Model Application No. 099200227 filed on Jan. 7, 2010, and the disclosures of the latter are incorporated by reference herein in their entirety.

CROSS-REFERENCES TO RELATED APPLICATIONS

Not applicable.

BACKGROUND OF THE INVENTION

1. Field of the Invention

The present invention relates to a buckling device, and more particularly, to a buckling device for fastening a belt.

2. Descriptions of the Related Art

When partaking in underwater activities, users must always wear masks and flippers. The mask may be a pair of swimming goggles, a pair of diving glasses or another kind of device for covering the facial contours of the users. Generally, both the mask and the flippers are provided with a buckling device and a belt so that the belt length can be adjusted according to the figure of each user. The belt is then fastened by the buckling device around the body of the user.

In references to FIGS. 1A to 1C, a conventional buckling device 1 comprises a body 11, a snap-fitting element 12, a resilient element 13, a first pivot 17 and a second pivot 16. The snap-fitting element 12 comprises an engaging end 15 and an opposite end 14. The opposite end 14 comes into contact with the resilient element 13, while the engaging end 15 engages with a belt (not shown) wound around the second pivot 16. When the user lifts the snap-fitting element 12 upwards, the opposite end 14 rotates inwards about the first pivot 17 to abut against the resilient element 13 (i.e., the snap-fitting element 12 shown in FIG. 1C rotates counterclockwise) so that the resilient element 13 is deformed outwards to generate a pre-pressing elastic restoring force. Also, the engaging end 15 tilts outwards to disengage from the belt of the mask, the flipper or the like. Then, the belt length can be adjusted according to the figure of the user to attach the mask, the flipper or the like to the user's body firmly and properly.

However, because the resilient element 13 is integrally formed with the body 11, the resilient element 13 needs to have sufficient strength, which tends to result in an insufficient flexibility of the material when the user applies a force to the opposite end 14. Consequently, the snap-fitting element 12 cannot be pulled outwards promptly by the user, so the user has to apply a great force when adjusting the belt. As a consequence, an excessive force is often applied by the user when directly pulling the snap-fitting element 12, thereby causing material fatigue or even fractures in the resilient element 13.

FIG. 2A to FIG. 2C depict another conventional buckling device 2. The buckling device 2 comprises a body 21, a snap-fitting element 22 and two push portions 24. The body 21 comprises a pivot 26, around which a belt (not shown) of a mask, a flipper or the like is adapted to be wound. The snap-fitting element 22 comprises a snap-fitting protrusion 23 and an engaging end 25. The two push portions 24 are disposed, opposite each other, on two sides (as shown in FIGS. 2A and 2B) of the snap-fitting element 22 along an axial direction of the pivot 26. The engaging end 25 is disposed on a side of the snap-fitting element 22 adjacent to the pivot 26 to abut against a belt (not shown) that is wound around the pivot 26. The snap-fitting protrusion 23 of the snap-fitting element 22 is snap-fitted with a hole of the body 21 so that the snap-fitting element 22 can obtain a resilient force. When the two push portions 24 simultaneously receive an inwards push force, the two edges of the snap-fitting element 22 are directly pushed by the push portions 24 to arch outwards so that a gap between the engaging end 25 and the belt of the mask, the flipper or the like is increased. Then, the length of the belt can be adjusted according to the figure of the user, and the belt can be wound around the user to attach the mask or the flippers to fit the user's body comfortably. Once the user releases the push portions 24, the snap-fitting element 22 returns to its original position by virtue of the resilient force of the snap-fitting protrusion 23. The push portions 24 also return to their original positions by means of a spring disposed between the push portions 24.

Similar to the aforesaid buckling device 1, as the snap-fitting protrusion 23 is integrally formed with the snap-fitting element 22, a sufficient strength and stiffness are required to engage with the belt. However, because the material of the snap-fitting protrusion 23 is too stiff, the snap-fitting protrusion 23 is also not flexible enough, making it difficult for the snap-fitting element 22 to arch outwards promptly when being pushed by the user and, therefore, leads to poor pushing tactility of the push portions 24 when the user adjusts the belt. As a consequence, an excessive force is often applied by the user when pushing the push portions 24, thereby also causing material fatigue or even fracture of the snap-fitting protrusion 23. Moreover, when the snap-fitting element 22 is directly pushed by the push portions 24 to arch outwards, violent friction occurs between the snap-fitting element 22 and the push portions 24, making them liable to wear. As a result of the wear, the engaging end 25 will fail to deliver a sufficient engagement force when engaging with the belt and cannot be securely pressed against the belt. Even worse, the belt may fall off during use, which would endanger the life of the user.

In view of this, an urgent need exists in the art to provide a buckling device which has good pushing tactility and is less liable to fatigue, fracture and wear.

SUMMARY OF THE INVENTION

An objective of the present invention is to provide a buckling device that is simple to assemble, has good pushing tactility and is less liable to fatigue, fracture and wear.

To achieve the aforesaid objective, a buckling device disclosed in the present invention is adapted to fasten a belt. The buckling device comprises a first portion, a second portion, an elastic portion and at least one push portion. The elastic portion is disposed between the first portion and the second portion. The second portion engages with the belt to fasten the belt. The at least one push portion is integrally formed with the elastic portion and exposed from the first portion and the second portion. The at least one push portion is adapted to be pushed inwards by an external force to force the elastic portion to extrude outwards so that the second portion is forced to move outwards to release the belt.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1A:
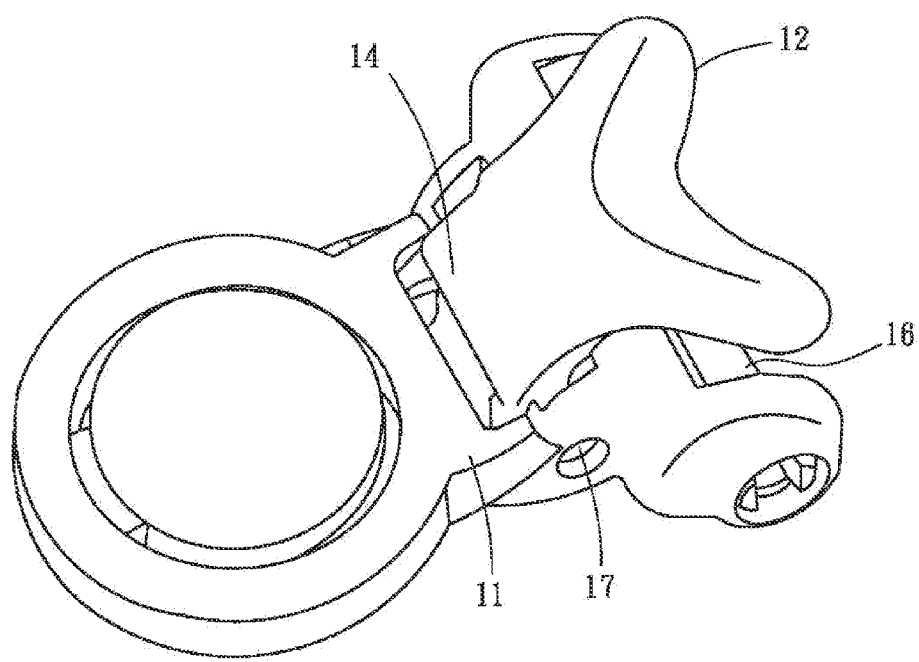
FIG. 1A is a schematic perspective view of a conventional buckling device.
Figure 1B:
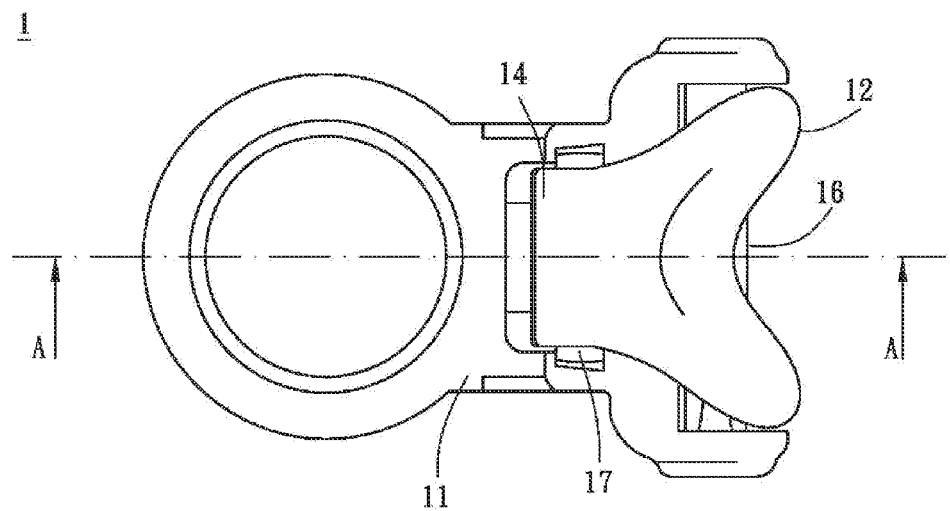
FIG. 1B illustrates a top view of the conventional buckling device.
Figure 1C:
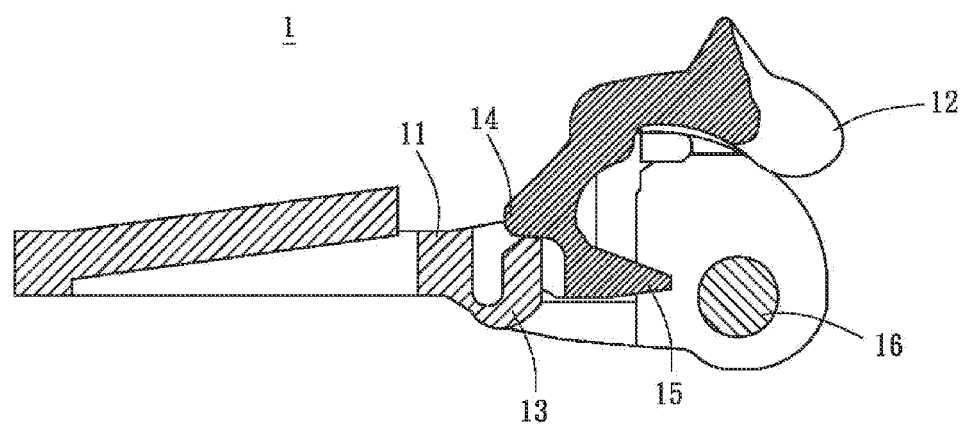
FIG. 1C is a schematic cross-sectional view of the conventional buckling device along line A-A.
Figure 2A:
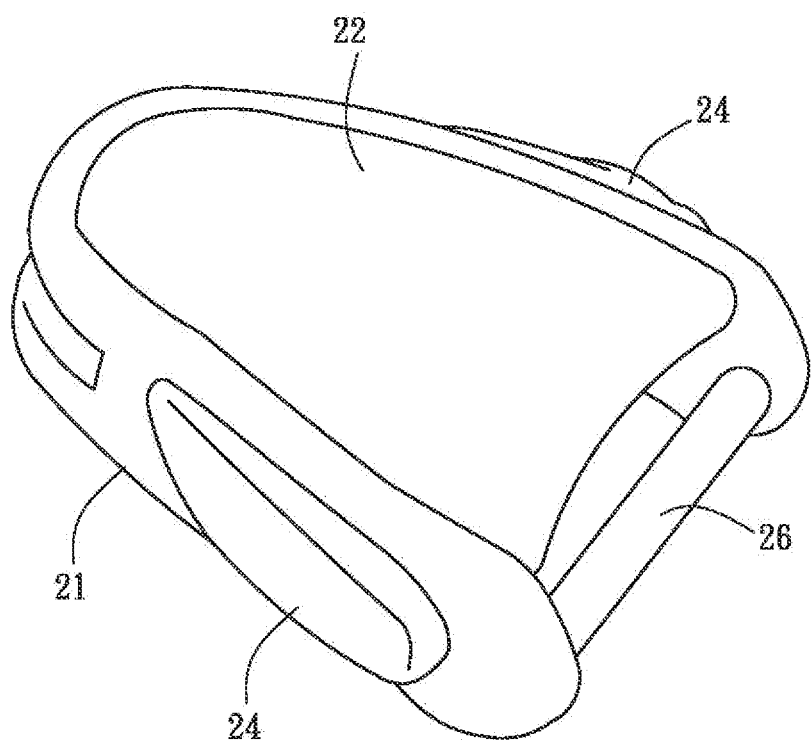
FIG. 2A is a schematic perspective view of another conventional buckling device.
Figure 2B:
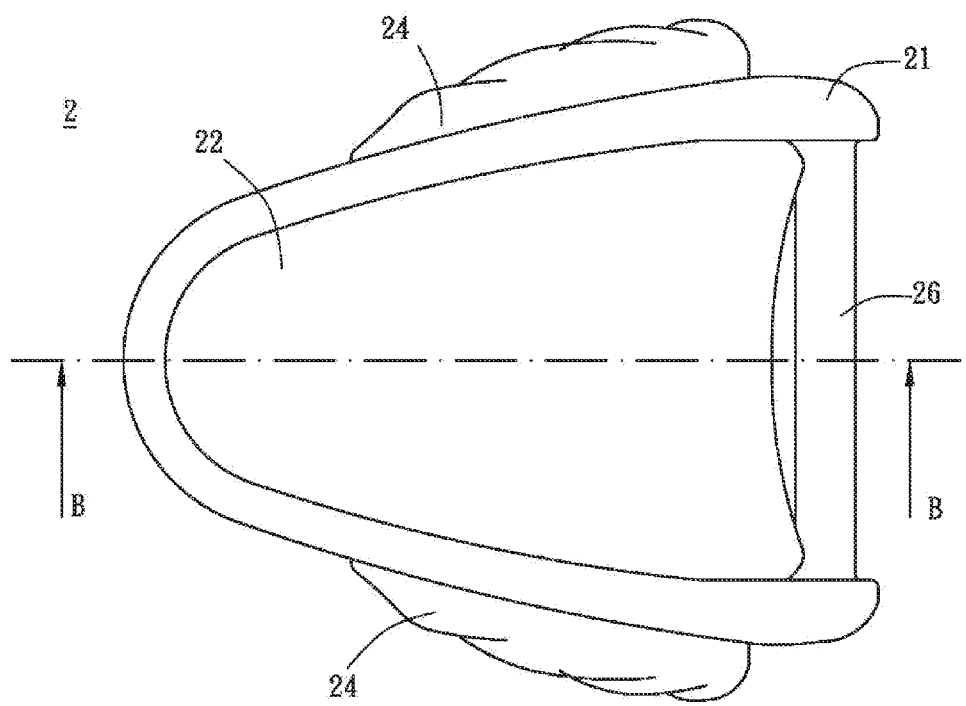
FIG. 2B illustrates a top view of the another conventional buckling device.
Figure 2C:
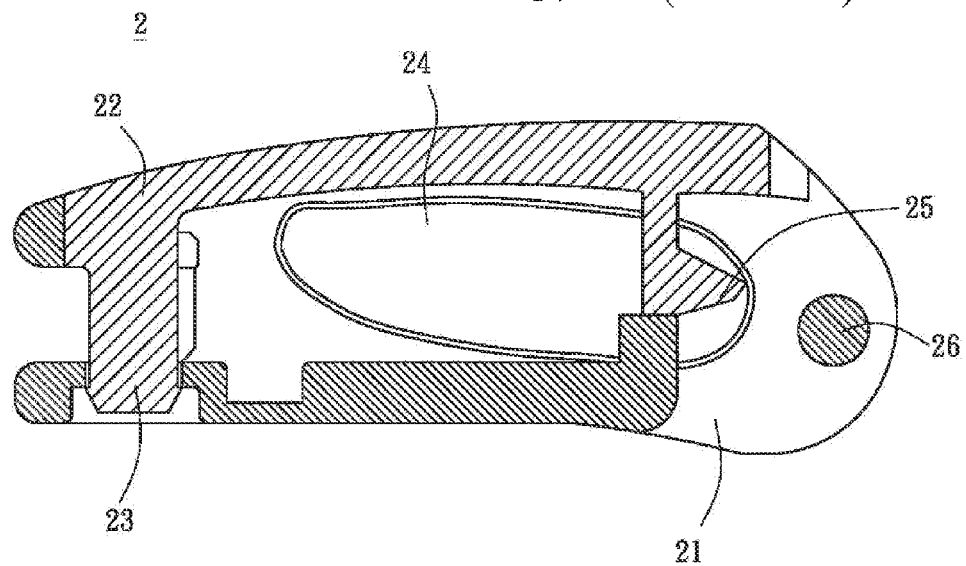
FIG. 2C is a schematic cross-sectional view of the another conventional buckling device along line B-B.

As shown in FIGS. 3A to 3D, a buckling device 3 according to the first embodiment of the present invention is adapted to fasten a belt 4. The buckling device 3 comprises a first portion 31, a second portion 32, an elastic portion 33 and at least one push portion 37. A pivot 36 of the buckling device 3 is fastened with the first portion 31, and the belt 4 is wound around the pivot 36. The elastic portion 33 is disposed between the first portion 31 and the second portion 32. The second portion 32 presses the belt 4 against the pivot 36 for purposes of fastening the belt 4.

It should be noted that in the present invention, the push portion 37 is integrally formed with the elastic portion 33 and exposed from the first portion 31 and the second portion 32. When the push portion 37 is pushed inwards by an external force to force the elastic portion 33 to deform and extrude outwards, the elastic portion 33 is adapted to force the second portion 32 to move outwards to release the belt 4 and disengage the second portion 32 from the belt 4, thereby allowing the user to adjust the belt 4 to a suitable length correspondingly.

More specifically, the second portion 32 of the buckling device 3 has an engaging end 322 and an opposite end 323 that is opposite the engaging end 322. The opposite end 323 is fastened with the first portion 31 so that when no force is exerted on the push portion 37 of the buckling device 3, the engaging end 322 is adapted to engage with and fasten the belt 4. The engaging end 322 of the second portion 32 has a first protrusion 321, while the opposite end 323 has a snap-fitting protrusion 323a. The first portion 31 has a snap-fitting hole 313 corresponding to the snap-fitting protrusion 323a, while the snap-fitting protrusion 323a of the opposite end 323 is adapted to be snap-fitted with the snap-fitting hole 313 to fixedly connect the first portion 31 and the second portion 32. Thereby, when the second portion 32 abuts against the elastic portion 33, the first protrusion 321 engages with a plurality of second protrusions 41 of the belt 4 to fasten the belt 4. Preferably, both the second protrusions 41 of the belt 4 and the first protrusion 321 are disposed parallel to the pivot 36 to facilitate adjustment of the length of the belt 4 by the user. Moreover, the snap-fitting protrusion 323a can be pivotally attached to other objects (e.g., masks or flippers) so that the buckling device 3, with the snap-fitting protrusion 323a as a pivot, can rotate with respect to other objects (e.g., masks or flippers).

Figure 3A:
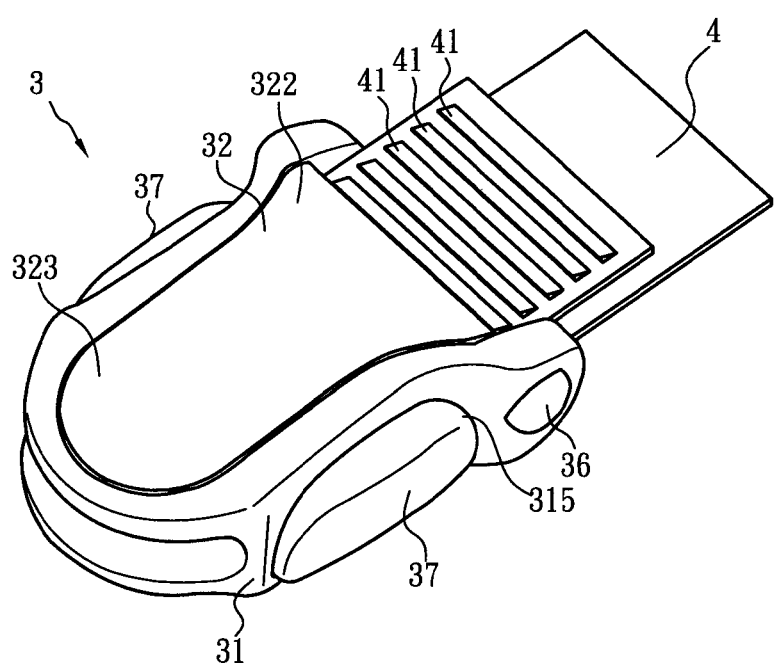
FIG. 3A is a schematic perspective view of a buckling device according to a first embodiment of the present invention.
Figure 3B:
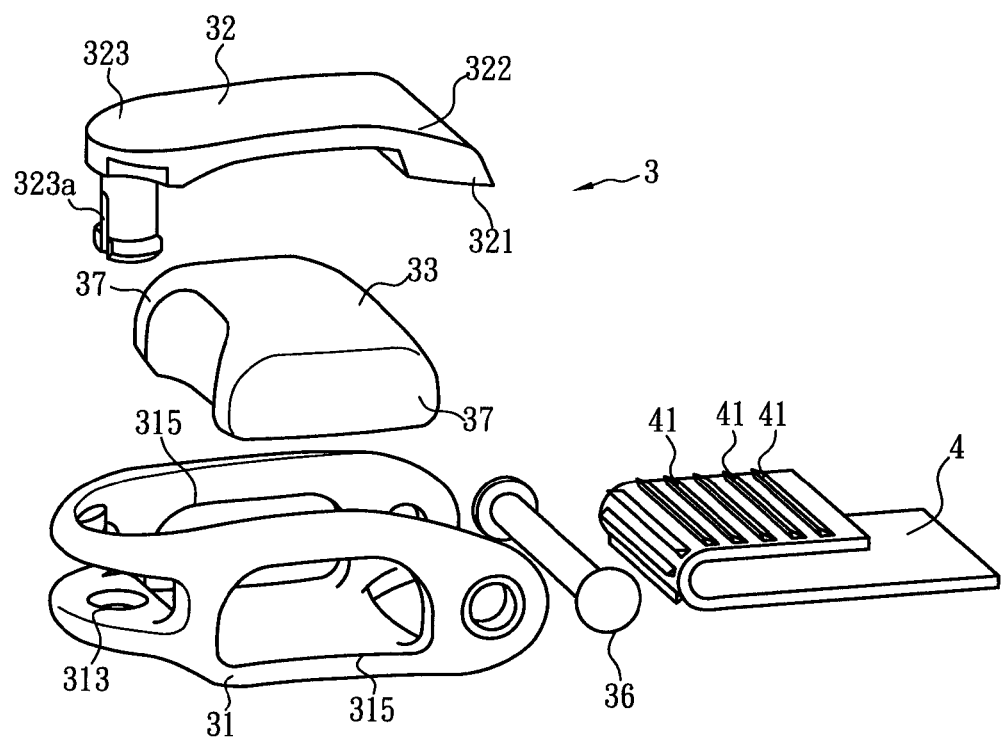
FIG. 3B is an exploded view of the buckling device according to the first embodiment of the present invention.
Figure 3C:
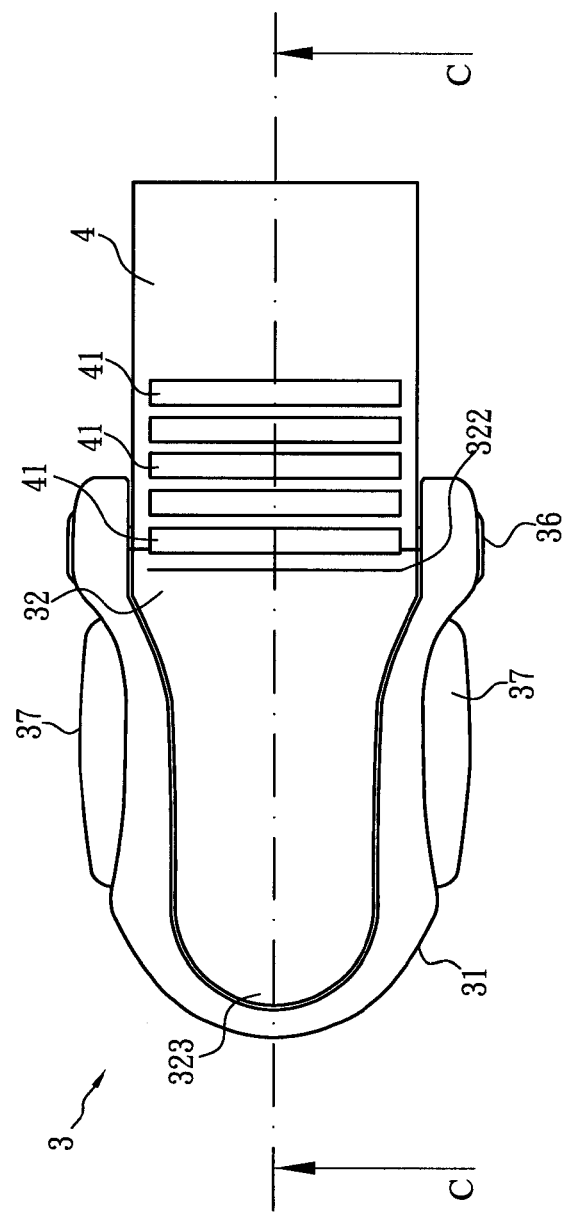
FIG. 3C illustrates a top view of the buckling device according to the first embodiment of the present invention.
Figure 3D:
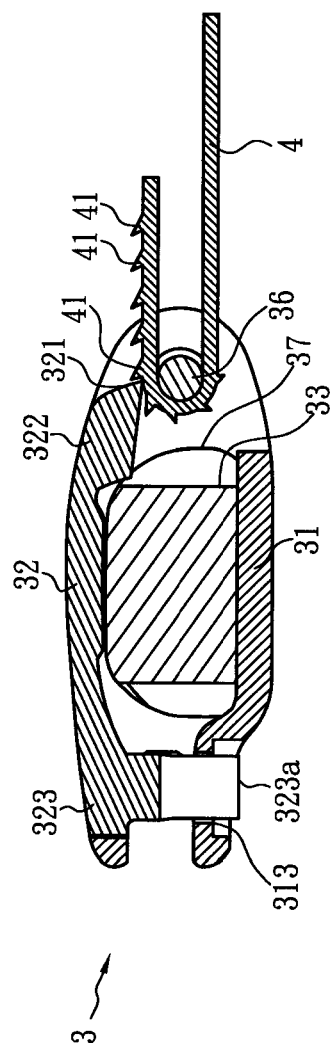
FIG. 3D is a schematic cross-sectional view of the buckling device along line C-C according to the first embodiment of the present invention.

As shown in FIGS. 3A and 3C, the buckling device 3 according to this embodiment of the present invention comprises two push portions 37, which are disposed on two sides of the second portion 32 and parallel to the axial direction of the pivot 36. The push portions 37 protrude from two openings 315 of the first portion 31 respectively to be exposed from the first portion 31 and the second portion 32. Now, a detailed process of adjusting the length of the belt 4 by using the buckling device 3 of the present invention will be described with references to both FIGS. 3B and 3D.

When pushed inwards simultaneously by a push force exerted by the user, the two push portions 37 will press and deform the elastic portion 33 so that it protrudes outwards. The protruded elastic portion 33 further pushes the engaging end 322 of the second portion 32 outwards to deform the second portion 32 so that the engaging end 322 rotates outwards with respect to the first portion 31 (i.e., the second portion 32 shown in FIG. 3D rotates counterclockwise). Thereby, a gap between the first protrusion 321 disposed on the engaging end 322 and the belt 4 is enlarged to release the second protrusion 41 of the belt 4. Then, the user can properly adjust the length of the belt 4 as needed to fasten a mask, a flipper or the like (not shown) to the body of the user.

Furthermore, when the second portion 32 is deformed to rotate the engaging end 322 outwards to release the second protrusion 41, an elastic restoring force is accumulated in each of the elastic portion 33, the push portions 37 integrally formed with the elastic portion 33 and the second portion 32. After the user has completed the adjustment of the length of the belt 4 and removed the push force exerted on the push portions 37, the elastic restoring force of the elastic portion 33 will be released to restore the protruded elastic portion 33 into its original shape. Then, the outward pushing action exerted on the second portion 32 by the elastic portion 33 disappears, and the elastic restoring force of the second portion 32 is released to restore the second portion 32 into its original shape. Correspondingly, the engaging end 322 rotates inwards with the movement of the second portion 32 (i.e., the second portion 32 shown in FIG. 3D rotates clockwise) to return back to its original position so that the first protrusion 321 disposed on the engaging end 322 engages with one of the second protrusions 41 of the belt 4 anew to re-fasten the belt 4.

Figure 4A:
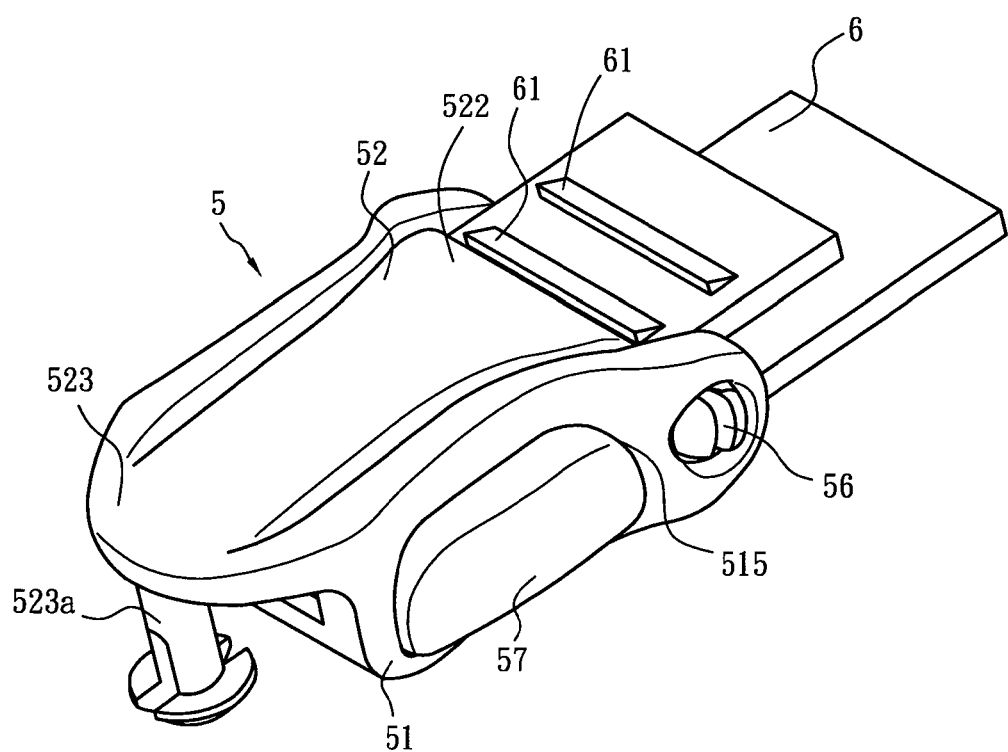
FIG. 4A is a schematic perspective view of a buckling device according to a second embodiment of the present invention.
Figure 4B:
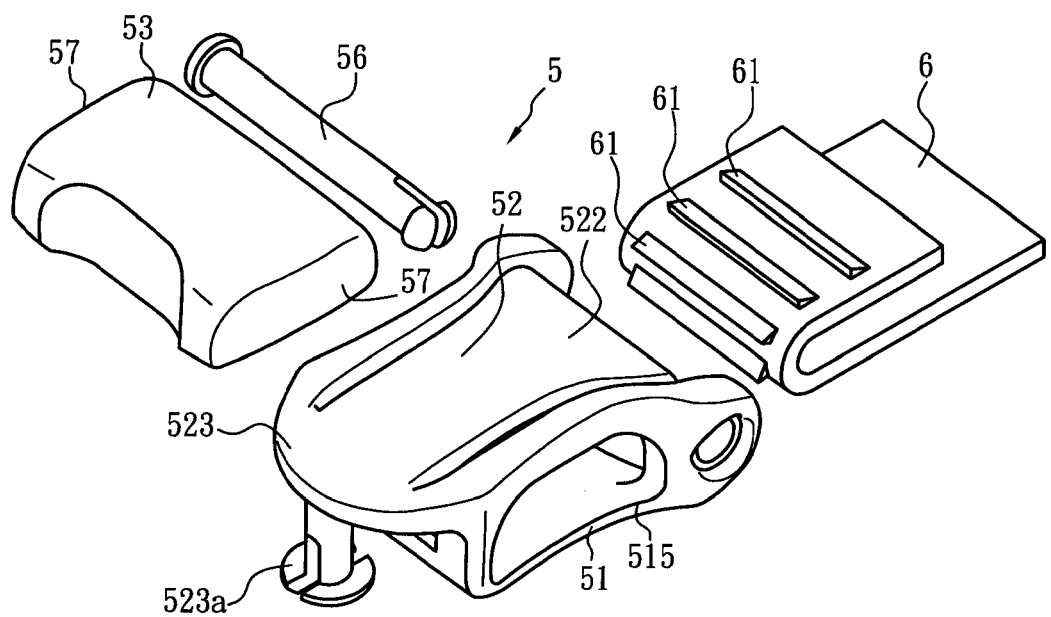
FIG. 4B is an exploded view of the buckling device according to the second embodiment of the present invention.
Figure 4C:
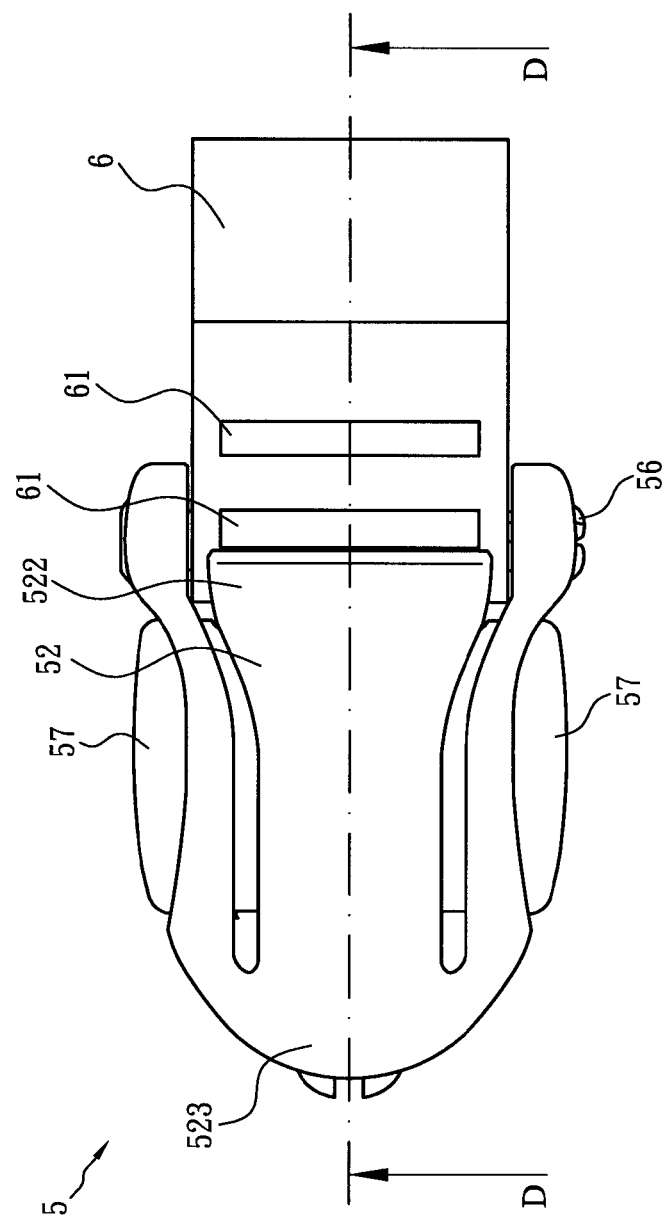
FIG. 4C is a top view of the buckling device according to the second embodiment of the present invention.
Figure 4D:
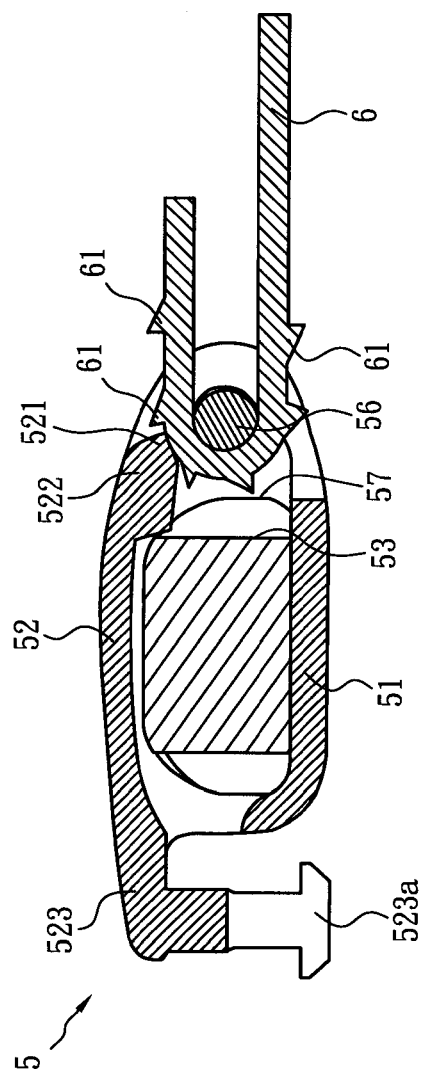
FIG. 4D is a schematic cross-sectional view of the buckling device along line D-D according to the second embodiment of the present invention.

Similar to the buckling device 3 of the first embodiment, a buckling device 5 according to the second embodiment of the present invention is adapted to fasten a belt 6, as shown in FIGS. 4A to 4D. Similar to the first embodiment, the buckling device 5 comprises a first portion 51, a second portion 52, an elastic portion 53 and at least one push portion 57. A pivot 56 of the buckling device 5 is fastened with the first portion 51, while the belt 6 is wound around the pivot 56. The elastic portion 53 is disposed between the first portion 51 and the second portion 52, while the second portion 52 presses the belt 6 against the pivot 56 for purposes of fastening the belt 6. As shown in FIGS. 4A and 4C, the buckling device 5, according to the second embodiment of the present invention, comprises two push portions 57, which are disposed on two sides of the second portion 52 and parallel to the axial direction of the pivot 56. The push portions 57 are integrally formed with the elastic portion 53 and exposed from the first portion 51 and the second portion 52. The push portions 57 protrude from two openings 515 of the first portion 51 respectively to be exposed from the first portion 51 and the second portion 52.

However, unlike the buckling device 3 of the first embodiment, the buckling device 5 of the second embodiment further has the first portion 51 and the second portion 52 integrally formed. With such a design, the cost of assembling the first portion 51 and the second portion 52 is saved for the buckling device 5 of the second embodiment. Because the first portion 51 and the second portion 52 of the buckling device 5 of the second embodiment are integrally formed, the first portion 51 does not need to be formed with the snap-fitting hole 313 of the first embodiment for snap-fitting with a snap-fitting protrusion 523a of the opposite end 523. The snap-fitting protrusion 523a of the second embodiment is only used to be pivotally fastened with other objects (e.g., masks or flippers) so that the buckling device 5 can, with the snap-fitting protrusion 523a as a pivot, rotate with respect to other objects (e.g., masks or flippers).

When pushed inwards simultaneously by push force exerted by the user, the two push portions 57 will deform and press the elastic portion 53 so that it protrude outwards. The protruded elastic portion 53 further pushes the engaging end 522 of the second portion 52 outwards to deform the second portion 52 so that the engaging end 522 rotates outwards with respect to the first portion 51 (i.e., the second portion 52 shown in FIG. 4D rotates counterclockwise). Thereby, a gap between the first protrusion 521 disposed on the engaging end 522 and the belt 6 is enlarged to release the second protrusion 61 of the belt 6. Then, the user can properly adjust the length of the belt 6 as needed to fasten a mask, a flipper or the like (not shown) to the body of the user.

Furthermore, when the second portion 52 is deformed to rotate the engaging end 522 outwards to release the second protrusion 61, an elastic restoring force accumulate in each of the elastic portions 53, the push portions 57 integrally formed with the elastic portions 53 and the second portion 52. After the user has completed the adjustment of the length of the belt 6 and removed the push force exerted on the push portions 57, the elastic restoring force of the elastic portion 53 will be released to restore the protruded elastic portion 53 into its original shape. Then, the outward pushing action exerted on the second portion 52 by the elastic portion 53 disappears, and the elastic restoring force of the second portion 52 is released to restore the second portion 52 into its original shape. Correspondingly, the engaging end 522 rotates inwards with the movement of the second portion 52 (i.e., the second portion 52 shown in FIG. 4D rotates clockwise) to return back to an original position so that the first protrusion 521 disposed on the engaging end 522 engages with one of the second protrusions 61 of the belt 6 anew to re-fasten the belt 6.

Figure 5:
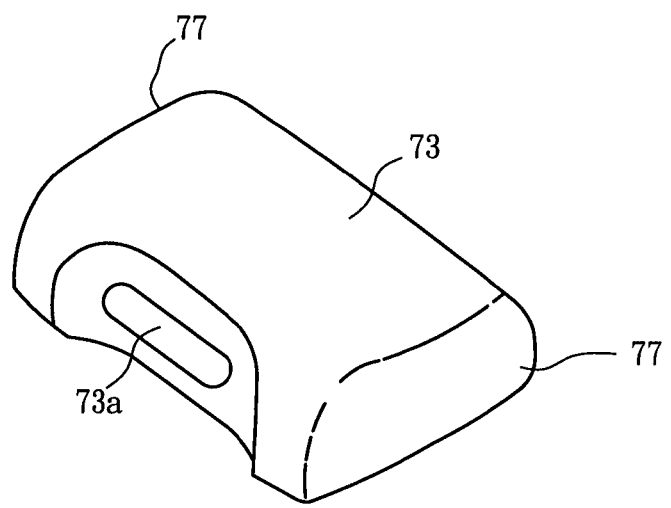
FIG. 5 is a schematic view illustrating an example where an elastic portion is formed with a hollow portion.

To adjust the extent of elasticity and deformation of the elastic portion of the aforesaid embodiment, as shown in FIG. 5, an elastic portion 73 may be formed with a hollow portion 73a in the middle portion thereof to make the elastic portion 73 easier to be deformed. When the push portions 77 are pushed inwards simultaneously by a push force exerted by the user, the elastic portion 73 is deformed and protrudes outwards to a certain extent, so that it can more easily push out the engaging ends 322, 522 of the second portions 32, 52.

In the aforesaid embodiments, the elastic portion and the push portions integrally formed with the elastic portion may both be made of a first material which has a Shore hardness substantially between A10 to A95, and the elastic portion has a coefficient of elasticity smaller than that of the first portion and lower than 20 Gpa; i.e., the elastic portion and the push portions have better flexibility than the first portion. The first material of the elastic portion and the push portions is preferably selected form the group consisting of silicone, Thermoplastic Rubber (TPR), Thermoplastic Elastomer (TPE), Polyvinyl Chloride (PVC), Natural Rubber, Synthetic Rubber and a combination thereof. The material of the first portion may be selected from the group consisting of Polycarbonate (PC), Alkylbenzene sulfonate (ABS), Polyoxymethylene (POM), Polypropylene (PP), Thermoplastic Rubber (TPR), Nylon, Polyethylene (PE), Polyurethane (PU) and a combination thereof.

Figure 6A:
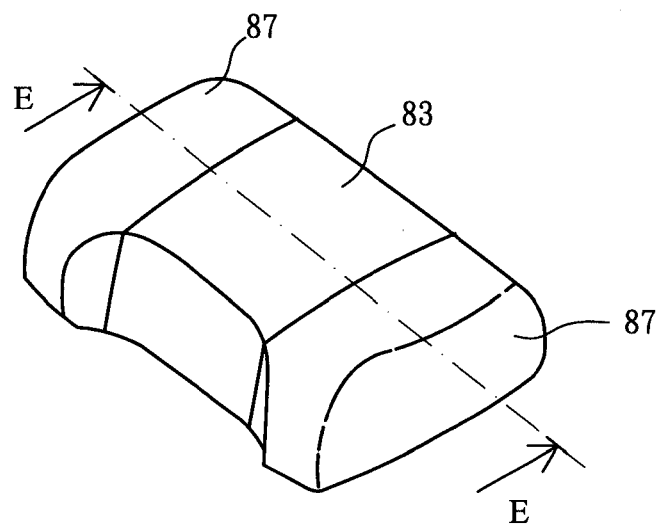
FIG. 6A is a schematic view illustrating an example where the elastic portion is harder than a push portion.
Figure 6B:
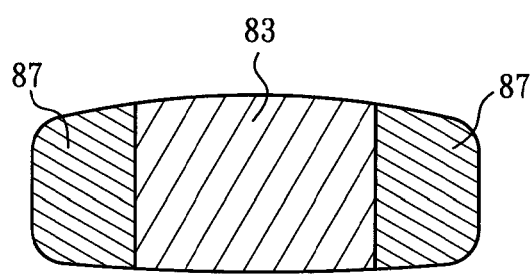
FIG. 6B is a schematic cross-sectional view along line E-E shown in FIG. 6A.
Figure 7A:
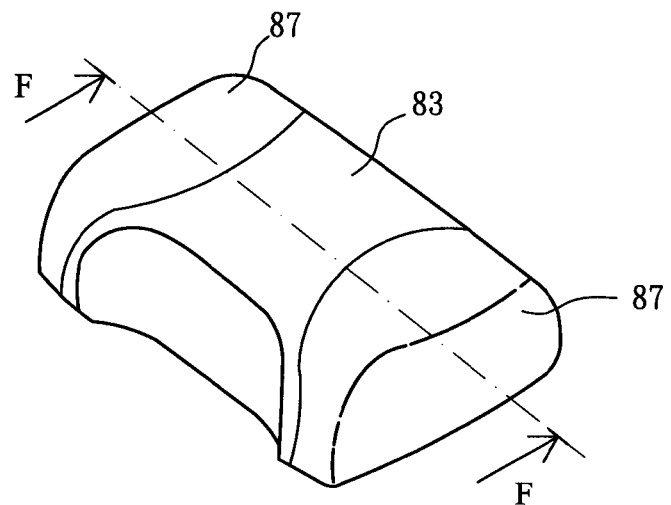
FIG. 7A is a schematic view illustrating an example where the elastic portion is softer than the push portion.
Figure 7B:
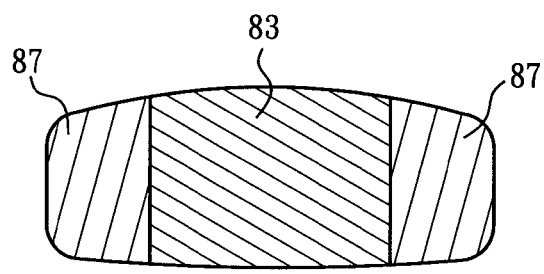
FIG. 7B is a schematic cross-sectional view along line F-F shown in FIG. 7A.
Figure 8A:
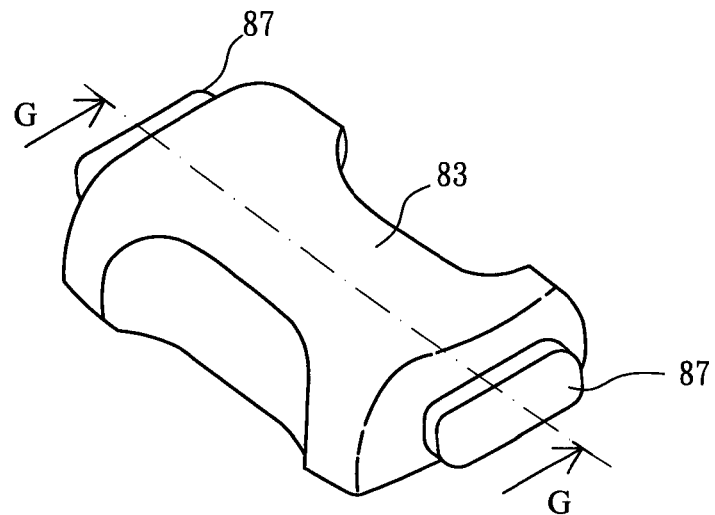
FIG. 8A is a schematic view illustrating another example where the elastic portion is softer than the push portion.
Figure 8B:
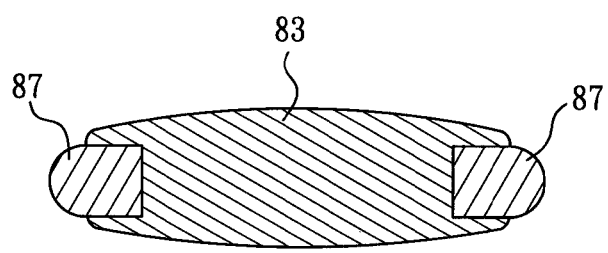
FIG. 8B is a schematic cross-sectional view along line G-G shown in FIG. 8A.

However, the elastic portion and the push portions described above may also be made of materials of different hardness. The elastic portion and the push portions may be made of the softer first material or the harder second material. For example, as shown in FIGS. 6A and 6B, an elastic portion 83 is made of the harder second material, while push portions 87 are made of the softer first material. In such a case, the second material of the elastic portion 83 is made of a high hardness silicone, while the elastic portion 83 is insert molded into the push portions 87, fastened with the push portions 87 through gluing or by other fastening means. For example, as shown in FIGS. 7A and 7B, in contrast, the elastic portion 83 is made of the softer first material, while the push portions 87 are made of the harder second material; in such a case, the second material is selected from the group consisting of Polyethylene (PE), Polycarbonate (PC), Acrylonitrile Butadiene Styrene (ABS), Polyoxymethylene (POM), Polypropylene (PP), Nylon, glass, high hardness silicone and a combination thereof, and the push portions 87 are insert molded into the elastic portion 83. For example, as shown in both FIGS. 8A and 8B, in a case where the elastic portion 83 is made of the softer first material and the push portions 87 are made of the harder second material, the push portions 87 may also be fastened with the elastic portion 83 through snap-fitting, inserting or gluing. Through the aforesaid variations in materials of the elastic portion 83 and the push portions 87, the tactility and deformation of the elastic portion 83 when the push portions 87 are pushed by the user to force the elastic portion 83 to protrude outwards can be greatly varied and adjusted depending on the requirements of users and the buckling device design.

Furthermore, because the elastic portion of the present invention is made of a material with good flexibility, it can be easily integrally formed with a soft portion of an object which is to be fastened by the belt. For example, the elastic portion may extend from a skirt portion of a mask and be integrally formed with the skirt portion. Alternatively, the elastic portion of the present invention may extend from a side edge of a flipper and be integrally formed with the side edge. The mask may be a pair of swimming goggles, diving glasses or another kind of device for covering the facial contours of the user, and are not merely limited thereto.

According to the above description, because the elastic portion of the buckling device of the present invention is made of a soft material with high flexibility, shortcomings such as elastic fatigue or fatigue fractures are eliminated and users can push the push portions and the elastic portion easily with a small force to operate the buckling device. The buckling device of the present invention also avoids the problems of the conventional buckling device that the conventional buckling device has poor pushing tactility and the user tends to apply an overlarge pushing force because only a portion of a hard component or only a metallic elastic component such as a spring is used as an elastic storage structure, and that further causes fatigue or fracture of the hard component that is used as the elastic storage structure. As a result, the device is not as fragile nor as prone to fractures, thereby, the buckling device of this invention obtains a prolonged service life. Moreover, by having push portions formed integrally with the elastic portion, the push portions can return back to the original position without need of a spring disposed therebetween. It should be noted that the positions, deformation directions, and materials of the elastic portion and the push portions, as well as the kinds of components that are integrally formed described in the aforesaid embodiments are not intended to limit the scope of the present invention, and those of ordinary skill in the art can proceed with other examples based on the same concepts as the present invention.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A buckling device for fastening a belt, comprising:
   a first portion;
   a second portion adapted to engage with the belt;
   an elastic portion disposed between the first portion and the second portion; and
   at least one push portion integrally formed with the elastic portion and exposed from the first portion and the second portion, in which the at least one push portion is adapted to be pushed in an inward direction by an external force to deform the elastic portion to in an upward and downward direction perpendicular to the inward direction to force the second portion to move outward to release the belt;
   wherein the first portion and the second portion form a space to accommodate the elastic portion, in which the first portion compromises at least one opening correspondingly receiving the at least one push portion, and
   wherein the first portion is made of a material selected from the group consisting of polycarbonate (PC), alkylbenzene sulfonate (ABS), polyoxymethylene (POM), polypropylene (PP), thermoplastic Rubber (TPR), nylon, polyethylene (PE), polyurethane (PU) and a combination thereof, and the elastic portion is made of a first material selected form the group consisting of silicone, Thermoplastic Rubber (TPR), Thermoplastic Polyurethane (TPU), Thermoplastic Elastomer (TPE), Polyvinyl Chloride (PVC), Natural Rubber, Synthetic Rubber and a combination thereof.

2. The buckling device as claimed in claim 1, wherein the second portion comprises an engaging end and an opposite end opposite to the engaging end, and the opposite end is fastened with the first portion while the engaging end is capable of engaging the belt.

3. The buckling device as claimed in claim 2, wherein the opposite end comprises a snap-fitting protrusion, the first portion comprises a snap-fitting hole, and the snap-fitting protrusion and the snap-fitting hole are snap-fitted together.

4. The buckling device as claimed in claim 2, wherein the first portion and the second portion are formed integrally.

5. The buckling device as claimed in claim 2, wherein the second portion comprises a first protrusion, the belt has a plurality of second protrusions, and the first protrusion is disposed on the engaging end to be capable of engaging the second protrusions of the belt.

6. The buckling device as claimed in claim 5, wherein the buckling device further comprises a pivot fastened with the first portion, and the pivot is capable of being wrapped with a belt.

7. The buckling device as claimed in claim 6, wherein the first protrusion is disposed parallel to the pivot, and the second protrusions is capable of being disposed parallel to the pivot.

8. The buckling device as claimed in claim 1, wherein the buckling device comprises two push portions, the first portion comprises two openings, and the push portions are protruded from the openings respectively.

9. The buckling device as claimed in claim 1, wherein the elastic portion is formed with a hollow portion.

10. The buckling device as claimed in claim 1, wherein the at least one push portion is made of a second material harder than the first material, and the first material has a shore hardness substantially between A10 to A95.

11. The buckling device as claimed in claim 1, wherein the at least one push portion is made of the first material.

\* \* \* \* \*